(12) United States Patent
Tian

(10) Patent No.: US 6,689,882 B2
(45) Date of Patent: Feb. 10, 2004

(54) PROCESS FOR THE SYNTHESIS OF MORPHOLINYLBENZENES

(75) Inventor: Wei Tian, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/276,011

(22) PCT Filed: May 14, 2001

(86) PCT No.: PCT/SE01/01064
§ 371 (c)(1), (2), (4) Date: Nov. 12, 2002

(87) PCT Pub. No.: WO01/87865
PCT Pub. Date: Nov. 22, 2001

(65) Prior Publication Data
US 2003/0171581 A1 Sep. 11, 2003

(30) Foreign Application Priority Data
May 18, 2000 (SE) ................................. 0001866

(51) Int. Cl.$^7$ .......................................... C07D 295/155
(52) U.S. Cl. ...................... 544/163; 544/169; 544/172; 544/175; 544/167
(58) Field of Search ................... 544/163, 169, 544/172

(56) References Cited

U.S. PATENT DOCUMENTS

| | | |
|---|---|---|
| 5,795,985 A | 8/1998 | Hüsler et al. |
| 5,817,877 A | 10/1998 | Hartwig et al. |
| 5,977,357 A | 11/1999 | Hüsler et al. |
| 6,191,182 B1 | 2/2001 | Hüsler et al. |

FOREIGN PATENT DOCUMENTS

JP  4089459  3/1992

OTHER PUBLICATIONS

Tetrahedron, vol 55, (38), 1999, p 11399–11428.
Tetrahedron, vol 55, (46), 1999, p 13285–13300.
Tetrahedron Letters, vol 40, (6), 1999, p 1219–1222.
Tetrahedron, vol 56, (24), 2000, p 4107.
Synthesis, 1990, 1145–1149.
Wolfe et al., J. Org. Chem., 1997, 62, 1264–1267.
Wolfe et al., J. Am. Chem. Soc., 1997, 119, 6054–6058.
Degutis, Yu. et al. J. Org. Chem. (USSR), 1978, 14, 1910–13 (in English).
Louie et al., J. Org. Chem., 1997, 62, 1268–73.
Tetrahedron Letters, vol 38, (36), 1997, 6363–6366.

*Primary Examiner*—Robert W. Ramsuer
(74) *Attorney, Agent, or Firm*—White & Case LLP

(57) ABSTRACT

A new improved process for synthesizing morpholinylbenzenes of the formula I by reacting morpholine of formula II with a substituted benzene of formula III, wherein morpholine is used as a reactant and as the only one solvent.

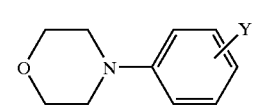

(I)

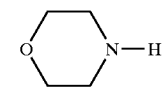

(II)

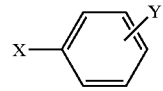

(III)

18 Claims, No Drawings

PROCESS FOR THE SYNTHESIS OF MORPHOLINYLBENZENES

FIELD OF THE INVENTION

The present invention relates to a new improved process for synthesizing morpholinylbenzenes, preferably 4-morpholinylbenzenes. There is a need for a simple and suitable large-scale synthesis possible to achieve high overall yield within an acceptable reaction time.

PRIOR ART

Tetrahedron letters, 1999, 40 (6), 1219–1222 and Tetrahedron, 1999, 55 (46), 13285–13300 disclose a process for synthesizing 4-(4-morpholinyl) benzonitrile and 4-(4-morpholinyl) benzoic acid ethyl ester by reacting morpholine and 4-fluorobenzonitril or ethyl 4-fluorobenzoate in the solvent dimethyl sulfoxide (DMSO).

Synthesis, 1990, 1145–1149 discloses a process for synthesizing 4-(4-morpholinyl) benzonitrile and 1-[4-(4-morpholinyl)phenyl] ethanone in the solvent acetonitrile under 10 kbar pressure. The reacting starting materials in said process are morpholine and 4-fluorobenzonitril or 1-(4-fluorophenyl) ethanone, respectively.

U.S. Pat. No. 5,817,877 discloses a method of preparing 4-(4-morpholinyl) benzonitrile in the presence of a palladium catalyst comprising a chelating ligand, in sodium t-butoxide (NaO-t-Bu) and toluene. The starting material in the process disclosed in U.S. Pat. No. 5,817,877 is morpholine and 4-cyanophenyltriflate.

EP 805152-B discloses a method of preparing 1-(4-morpholinophenyl) alkylketone by reaction of morpholine and the corresponding 1-(4-bromophenyl) alkylketone in aqueous solution under 5–6 bar pressure.

JP 04089459 discloses a method of preparing 4-(4-nitrophenyl) morpholine and 2-(4-nitrophenyl) morpholine by reaction of morpholine and 4-(4-nitrophenyltriflate) morpholine or 4-(4-nitrophenyl triflate) morpholine, respectively, in acetonitrile.

DISCLOSURE OF THE INVENTION

This invention discloses a nucleophile aromatic amination method different from all those previously disclosed methods in the prior art. The process of the present invention does not need any additional solvent, it uses morpholine as the reactant and as the only one solvent, if a solvent is present.

The object of the present invention is to provide a new and improved process to synthesize 4-(4-morpholinyl) benzene and 2-(4-morpholinyl) benzene of the formula I.

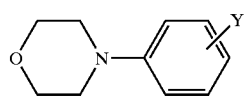

This invention discloses a simple and improved method to synthesize morpholinylbenzene of the formula I

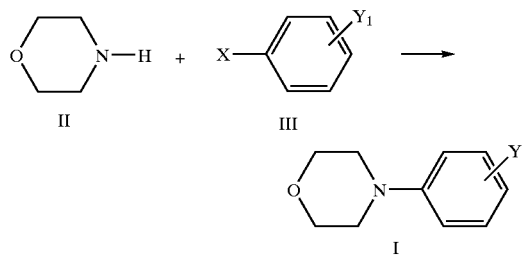

by reacting morpholine of formula II with a substituted benzene of formula III, wherein Y and $Y_1$ are a substituent in 2- or 4-position and
Y is $Y_1$ or COOH,
$Y_1$ is CN, $NO_2$, $CF_3$, $COOR^1$, $COR^1$ and $CONR^2R^3$,
where $R^1$ is H, $C_{1-6}$ alkyl, $C_{3-6}$ cycloalkyl, $C_{1-6}$ alkyl$C_{3-6}$ cycloalkyl, $C_6$–$C_{10}$ aryl or a heterocyclic ring containing one or two heteroatoms selected from N, O, S, and said heterocyclic ring may optionally be substituted;
where $R^2$, $R^3$ is H, $C_{1-6}$ alkyl, $C_{3-6}$ cycloalkyl, $C_{1-6}$ alkyl$C_{3-6}$ cycloalkyl and $C_6$–$C_{10}$ aryl or heterocyclic ring containing one or two heteroatoms selected from N, O, S, and said heterocyclic ring may optionally be substituted, or may together with the nitrogen atom form a heterocyclic ring;
with the provisio that $Y_1$ is not COOH;
X is a leaving group;
characterized in that the morpholine is used as a reactant and as the only one solvent, if solvent is present;
and, if necessary, hydrolysis to form a compound wherein Y is COOH.

A preferred embodiment of the present invention is an improved process for the synthesizing of morpholinylbenzene of formula I, wherein Y is COOH starting from a morpholinylbenzene of formula I, wherein Y is $Y_1$, where $Y_1$ is $COCH_3$ followed by a haloform reaction or $Y_1$ is CN, $CONH_2$, $COOC_2H_5$ followed by basic hydrolysis but an acid hydrolysis is possible as well. Particularly preferred is, when the whole process is performed using one pot without any isolation of the product before the hydrolysis.

Another preferred embodiment of the present invention is an improved process for the synthesizing of morpholinylbenzene of formula L wherein Y is CN, $CONH_2$, $COOC_2H_5$, $COCH_3$, COOH and $NO_2$, by reacting morpholine of formula II with a substituted benzene of formula III, wherein X is F, Cl, Br or $CF_3SO_3$, preferably F and $Y_1$ is CN, $CONH_2$, $COOC_2H_5$, $COCH_3$ and $NO_2$.

Another preferred embodiment of the present invention is an improved process for the synthesizing of morpholinylbenzene of formula I, wherein Y is $NO_2$, by reacting morpholine of formula II with a substituted benzene of formula III, wherein X is F and $Y_1$ is $NO_2$.

A preferred embodiment of the present invention is an improved process for the synthesizing of morpholinylbenzene of formula I, wherein the electron-withdrawing group Y is in the 4-position.

A preferred embodiment of the present invention is an improved process for the synthesizing of morpholinylbenzene of formula I, wherein the molar ratio of the reactant morpholine to substituted benzene may be up to 10:1, preferably in the ranges from 6,7:1 to 1:1, more preferably from 3.5:1 to 1:1. No excess of morpholine (molar ratio 1:1) is needed when $Y_1$ is $NO_2$ After the conversion of morpholinylbenzenes is completed the aqueous mixture is made basic by a base, such as NaHCO₃, if the molar ratio of morpholine to substituted benzene in the reaction is 1:1. This is to keep the product from being protonated by HX, which is generated during the reaction. The crude product may be used without working-up or isolation as a starting material for the next reaction.

In the present context $C_1$–$C_6$ alkyl may be straight or branched. $C_1$–$C_6$ alkyl may be methyl, ethyl, n-propyl, i-propyl, n-butyl, i-butyl, s-butyl, t-butyl, n-pentyl, i-pentyl, t-pentyl, neo-pentyl, n-hexyl or i-hexyl.

In the present context $C_3$–$C_6$ cycloalkyl may be cyclopropyl, cyclobutyl, cyclopentyl, cyclohexyl. $C_{1-6}$ alkyl$C_{3-6}$ cycloalkyl may be methylcyclopropyl, ethylcyclopropyl, methylcyclobutyl, ethylcyclobutyl, or methylcyclopentyl.

In the present context $C_6$–$C_{10}$ aryl may be a phenyl or a naphthyl, which groups may optionally be substituted.

In the present context a heterocyclic ring containing one or two heteroatoms selected from O, S, N, is preferably a 5- or 6-membered ring for example imidiazolidinyl, imidiazolinyl, morpholinyl, piperazinyl, piperidinyl, piperonidyl, pyrazolidinyl, pyrazolinyl, pyrrolidinyl, pyrrolinyl, tetrahydropyranyl, thiomorpholinyl, preferably, piperidino, 1-piperazinyl, morpholino, thiomorpholino and 4-piperidon-1-yl.

X is a leaving group, preferably halogen such as F, Cl, Br, I or CF₃SO₃, particularly preferred is F.

Both pure enantiomers and racemic mixture of the compounds of formula I is within the scope of the present invention.

In the present context a base may be alkali metal carbonates such as a sodium carbonate and a potassium carbonate, or alkali metal hydrogen carbonates such as a sodium hydrogen carbonate and a potassium hydrogen carbonate, or alkali metal hydroxides such as a sodium hydroxide and a potassium hydroxide, or amines such as an alkylamines, e.g. triethylamine, diethylamine, ethanolamine. Other possible bases known to a person skilled in the art may be used, too. Sodium hydrogen carbonate is one of the preferred bases.

DETAILED DESCRIPTION OF THE INVENTION

A mixture of the two reagents, morpholine and the substituted benzene is gently warmed up. The reaction temperature may vary for example from 20° C. to 130° C., preferably from 40° C. up to 120° C., depending on the nature of the electron withdrawing group $Y_1$. A low reaction temperature of about 40° C. is typically when $Y_1$ is $NO_2$, a reaction temperature of about 120° C. is typically when Y, is CN, CONH₂, COOC₂H₅ or COCH₃.

The reaction times may vary for example between 0.5 hours to 72 hours, preferably 0.5 hours to 36 hours, depending on the nature of the electron withdrawing group $Y_1$. After the reaction is completed, water is added into the reaction mixture. In most cases, the product 4-morpholinylbenzene of formula I precipitates from the aqueous solution, and is collected by filtration.

The present invention discloses a process to prepare 4-(4-morpholinyl) benzoic acid, directly from the halobenzene derivative by a two step process as shown below. The product from the first step is directly hydrolyzed in the same reactor in the second step to obtain a high yield of the 4-(4-morpholinyl) benzoic acid. This is defined as a one-pot method. A basic hydrolysis is preferred in the second step, preferably with sodium hydroxide, but acid hydrolysis is possible.

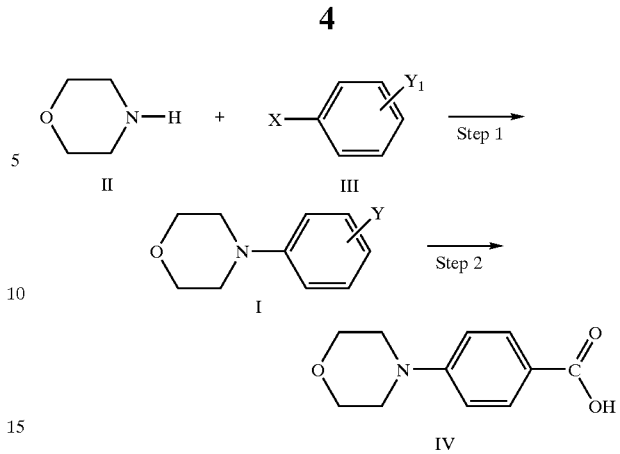

This object is achieved by the process of the present invention, which is characteterized in that the morpholine is used as a reactant and as the only one solvent. This advantageously avoids the use of catalyst and base over processes known in the art. Further advantageous is, that the process of the invention produces good yields under mild conditions, such as normal pressure. However, to work under pressure will also function.

Compounds of formula I, wherein Y is an electron-withdrawing group such as a nitrile, cyano, trifluormethyl, carboxylic ester, ketone or amide group, are useful intermediates. They are widely used as building blocks in the synthesis of new drugs. An efficient method for the preparation of these compounds is therefore very desirable and of commercial value.

EXAMPLES

This invention is further illustrated by the following examples.

Example 1

Preparation of 4-(4-morpholinyl) Benzonitrile:

A mixture of morpholine (50 g, 0.6 mol) and 4-fluorobenzonitrile (24 g, 0.2 mol) is heated at 120° C. The conversion of the 4-fluorobenzonitrile is complete after 5 hours. Water (10 ml) is then added into the reaction mixture. The precipitate is filtered off, washed with water and dried under vacuum (30° C.) to give 37 g of the title-compound. Yield: 95%; m.p. 82–83° C.; MS 188 (100, M⁺); H¹ NMR (CDCl₃): δ 7.46 (dd, 2H), 6.81 (dd, 2H), 3.79 (t, 4H), 3.22 (t, 4H); C¹³ NMR (CDCl₃): δ 153.69, 133.71, 120.07, 114.26, 101.16, 66.65, 47.49.

Example 2

Preparation of 4-(4-morpholinyl) Benzonitrile:

A mixture of morpholine (3 g, 34 mmol) and 4-chlorobenzonitrile (1.55 g, 11.2 mmol) is heated at 120° C. The conversion of the 4-chlorobenzonitrile is complete after 12 hours. Water (10 ml) is then added into the reaction mixture. The precipitate is filtered off, washed with water and dried under vacuum (30° C.). Recrystallisation (50% aqueous ethanol) of the dried crude product gives 1.1 g of the title-compound. Yield: 52%, m.p. 82–83° C.; MS 188 (100, M⁺); H¹ NMR (CDCl₃): δ 7.46 (dd, 2H), 6.81 (dd, 2H), 3.79 (t, 4H), 3.22 (t, 4H); C¹³ NMR (CDCl₃): δ 153.69, 133.71, 120.07, 114.26, 101.16, 66.65, 47.49.

Example 3

Preparation of 4-(4-morpholinyl) Benzonitrile:

A mixture of morpholine (3 g, 34 mmol) and 4-bromobenzonitrile (1.95 g, 10.7 mmol) is heated at 120°

C. The conversion of the 4-bromobenzonitrile is complete after 24 hours. Water (10 ml) is then added into the reaction mixture. The precipitate is filtered off, washed with water and dried under vacuum (30° C.). Recrystallisation (50% aqueous ethanol) of the dried crude product gives 1.2 g of the title-compound. Yield: 65%, m.p. 82–83° C.; MS 188 (100, M$^+$); H$^1$ NMR (CDCl$_3$): δ 7.46 (dd, 2H), 6.81 (dd, 2H), 3.79 (t, 4H), 3.22 (t, 4H); C$^{13}$ NMR (CDCl$_3$): δ 153.69, 133.71, 120.07, 114.26, 101.16, 66.65, 47.49.

Example 4
Preparation of 4-(4-morpholinyl) Benzonitrile:
A mixture of morpholine (3 g, 34 mmol) and the freshly prepared 4-[(trifluoromethyl)sulfonyl] benzonitrile (1.2 g, 5.1 mmol, Ref.: A. M. Echavarren and J. K. Stille, J. Am. Chem. Soc. 1987, 109, 5478–5486.), is heated at 120° C. The conversion of the 4-[(trifluoromethyl)sulfonyl] benzonitrile is complete after 20 hours. Water (10 ml) is than added into the reaction mixture. The precipitate is filtered off, washed with water and dried under vacuum (30° C.). Recrystallisation (50% aqueous ethanol) of the dried crude product gives 0.5 g of the title-compound. Yield: 52%, m.p. 82–83° C.; MS 188 (100, M$^+$); H$^1$ NMR (CDCl$_3$): δ 7.46 (dd, 2H), 6.81 (dd, 2H), 3.79 (t, 4H), 3.22 (t, 4H); C$^{13}$ NMR (CDCl$_3$): δ 153.69, 133.71, 120.07, 114.26, 101.16, 66.65, 47.49.

Example 5
Preparation of 4-(4-morpholinyl) Benzamide:
A mixture of morpholine (2.0 g, 0.23 mmol) and 4-fluorobenzamide (1.2 g, 8.6 mmol) is heated at 120° C. The conversion of the 4-fluorobenzoamide is complete after 10 hours. Water (10 ml) is than added into the reaction mixture. The precipitate is filtered off, washed with water and dried under vacuum (30° C.) to give 1.6 g of the title-compound. Yield: 94%; m.p. 220–221° C.; MS 206 (100, M$^+$); H$^1$ NMR (DMSO): δ 7.76 (d, 2H), 7.75 (b, 1H), 7.05 (b, 1H), 6.94 (d, 21H), 3.73 (t, 4H), 3.20 (t, 4H); C$^{13}$ NMR (CDCl$_3$): δ 167.61, 152.90, 128.79, 123.93, 113.31, 65.92, 47.36.

Example 6
Preparation of 4-(4-morpholinyl) Benzoic Acid Ethyl Ester:
A mixture of morpholine (12 g, 0.14 mol) and ethyl 4-fluorobenzoate (8 g, 0.04 mol) is heated at 120° C. The conversion of the 4-fluorobenzoate is complete after 24 hours. Water (10 ml) is than added into the reaction mixture. The precipitate is filtered off, washed with water and dried under vacuum (30° C.) to give 9.2 g of pure 4-(4-morpholinyl) benzoic acid ethyl ester after recrystallisation from aqueous ethanol (50%, v/v). Yield: 89%. m.p. 82–83° C.; MS 235 (100, M$^+$); H$^1$ NMR (CDCl$_3$): δ 7.93 (d, 21H), 6.86 (dd, 2H), 4.33 (q, 2H), 3.85 (t, 4H), 3.28 (t, 4H), 1.37 (t, 311); C$^{13}$ NMR (CDCl$_3$): δ 166.57, 154.14, 131.14, 120.70, 113.46, 66.60, 60.39, 47.75, 14.40.

Example 7
Preparation of 1-[4-(4-morpholinyl)phenyl] Ethanone:
A mixture of morpholine (3.2 g, 37 mmol) and 1-(4-fluorophenyl) ethanone (1.5 g, 11 mmol) is heated at 120° C. The conversion of the 1-(4-fluorophenyl) ethanone is complete after 10 hours. Water (10 ml) is than added into the reaction mixture. The precipitate is filtered off, washed with water and dried under vacuum (30° C.) to give 2.1 g of the title-compound. Yield: 93%; m.p. 95–96° C.; MS 205 (100, M$^+$); H$^1$ NMR (CDCl$_3$): δ 7.99 (d, 2H), 6.86 (d, 2H), 3.86 (t, 4H), 3.30 (t, 4H), 2.53 (s, 3H); C$^{13}$ NMR (CDCl$_3$): δ 196.76, 154.43, 130.55, 128.36, 113.48, 101.16, 66.7, 47.73, 26.37.

Example 8
Preparation of 4-(4-nitrophenyl) Morpholine:
A mixture of morpholine (1.0 g, 11 mmol) and 1-fluoro-4-nitrobenzene (1.48 g, 10.5 mmol) is heated at 40° C. The conversion of 4-(4-nitrophenyl)morpholine is complete after 30 min. Cold water (10 ml) is added into the reaction mixture and the aqueous mixture is made pH 8 by the addition of saturated NaHCO$_3$. The yellow precipitate is filtered off, washed with water and dried under vacuum (30° C.) to give 2.0 g of the title-compound after recrystallisation from 70% ethanol. Yield: 95%; m.p. 152–153° C.; MS 208 (100, M$^+$); H$^1$ NMR (CDCl$_3$): δ 8.13 (d, 2H), 6.82 (d, 2H), 3.86 (t, 4H), 3.36 (t, 4H); C$^3$ NMR (CDCl$_3$): δ 154.95, 138.94, 125.84, 112.58, 66.32, 47.08.

Example 9
Preparation of 4-(2-nitrophenyl) Morpholine:
A mixture of morpholine (0.9 g, 10.03 mmol) and 1-fluoro-2-nitrobenzene (1.41 g, 10 mmol) is heated at 40° C. The conversion of 4-(2-nitrophenyl)morpholine is complete after 1 h. Cold water (10 ml) and diethylether (10 ml) are added into the reaction mixture and the aqueous mixture is made pH 8 by the addition of saturated NaHCO$_3$. The organic phase is separated from the water phase. The product is obtained as a syrup after the removal of the diethylether and gives 2.0 g of the title-compound. Yield: 96%; MS 208 (100, M$^+$); H$^1$ NMR (CDCl$_3$): δ 7.77 (dd, 1H), 7.52 (dt, 1H), 7.13 (dd, 1H), 7.07 (dt, 1H), 3.83 (dt, 4H), 3.05 (t, 4H); C$^3$ NMR (CDCl$_3$): δ 145.77, 143.67, 133.54, 125.86, 122.26, 120.87, 66.82, 52.05.

Example 10
Preparation of 4-(4-morpholinyl) Benzoic Acid Staring From 4-fluorobenzonitrile by the One-Pot Method Using Basic Hydrolysis:
A mixture of 4-fluorobenzonitrile (5.04 g, 41.6 mmol) and morpholine (9.12 g, 104.6 mmol) is heated at 120° C. to achieve a complete conversion of 4-fluorobenzonitrile after 5 hours. Water (100 ml) and NaOH (4.1 g, 10 mmol) are added to the reaction mixture. The whole mixture is kept refluxing for another 5 h, cooled down to room temperature and made acidic by the addition of HCl (5%) with efficient stirring. The precipitate is filtered off, washed with water and dried under vacuum (60° C.) to give 8.34 g of the title-compound. Yield: 99%; m.p. 275–277° C.; MS 207 (100, M$^+$); H$^1$ NMR (DMSO): 12.33 (b, 1H), 7.78 (d, 2H), 6.95 (d, 2H), 3.72 (t, 2H), 3.23 (t, 2H); δ C$^3$ NMR (CDCl$_3$): δ 167.25, 153.90, 130.81, 119.91, 113.22, 65.87, 46.97.

Example 11
Preparation of 4-(4-morpholinyl) Benzoic Acid Staring From Ethyl 4-fluorobenzoate by the One-Pot Method Using Basic Hydrolysis:
A mixture of ethyl 4-fluorobenzoate (3.5 g, 21 mmol) and morpholine (6.2 g, 70 mmol) is heated at 130° C. to achieve complete conversion of ethyl 4-fluorobenzoate after 12 hours. Water (15 ml) and NaOH (20%, 10 ml) are added to the reaction mixture. The whole mixture is then kept refluxing for another 3.5 hours, cooled down to room temperature and made acidic by the addition of HCl (5%) with efficient stirring. The precipitate is filtered off, washed with water and dried under vacuum (60° C.) to give 3.9 g of the title-compound. Yield: 90%, m.p. 275–277° C.; MS 207 (100, M$^+$); H$^1$ NMR (DMSO): 12.33 (b, 1H), 7.78 (d, 2H), 6.95 (d, 2H), 3.72 (t, 2H), 3.23 (t, 2H); δ C$^3$ NMR (CDCl$_3$): δ 167.25, 153.90, 130.81, 119.91, 113.22, 65.87, 46.97.

Example 12
Preparation of 4-(4-morpholinyl) Benzoic Acid Staring From 4-fluorobenzonitrile by the One-Pot Method Using Acidic Hydrolysis:

A mixture of 4-fluorobenzonitrile (1.11 g, 9.17 mmol) and morpholine (0.8 g, 9.19 mmol) is heated at 120° C. to achieve a complete conversion of ethyl 4-fluorobenzonitrile after 5 hours. Hydrochloric acid (10 ml, 20%) is then added into the reaction mixture. The whole mixture is then kept refluxing for another 15 hours, cooled down to room temperature and made pH 2 by the additon of NaOH (10%). The precipitate is filtered off, washed with water and dried under vacuum (60° C.) to give 1.5 g of the title-compound. Yield: 80%, m.p. 275–277° C.; MS 207 (100, M$^+$); H$^1$ NMR (DMSO): 12.33 (b, 1H), 7.78 (d, 2H), 6.95 (d, 2H), 3.72 (t, 2H), 3.23 (t, 2H); δ C$^3$ NMR (CDCl$_3$): δ 167.25, 153.90, 130.81, 119.91; 113.22, 65.87, 46.97.

What is claimed is:

1. An improved process for synthesizing a 4-morpholinylbenzene compound of formula I, by

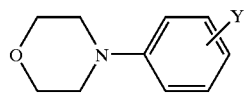

reacting morpholine of formula II with a substituted benzene of formula III and optionally performing hydrolysis to obtain the compound of Formula I wherein Y is COOH,

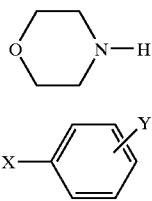

wherein
X is a leaving group;
Y and Y$_1$ are substituent in the 2- or 4-position;
Y is Y$_1$ or COOH; and
Y$_1$ is CN, NO$_2$, CF$_3$, COOR$^1$, COR$^1$, or CONR$^2$R$^3$
where R$^1$ is selected from the group consisting of H, C$_{1-6}$ alkyl, C$_{3-6}$ cycloalkyl, C$_{1-3}$ alkylC$_{3-6}$ cycloalkyl, C$_6$–C$_{10}$ aryl, and an unsubstituted or optionally-substituted heterocyclic ring containing one or two heteroatoms selected from N, O, S;
R$^2$, R$^3$ are selected from the group consisting of is H, C$_{1-6}$ alkyl, C$_{3-6}$ cycloalkyl, C$_{1-3}$ alkylC$_{3-6}$ cycloalkyl, C$_6$–C$_{10}$ aryl and an unsubstituted or optionally-substituted heterocyclic ring containing one or two heteroatoms selected from N, O, S, or R$^2$ and R$^3$ may together with the nitrogen atom to which they are attached form a heterocyclic ring;
with the provisio that Y, is not COOH,
and wherein the morpholine is used as reactant and sole solvent, if solvent is optionally present.

2. The process according to claim 1, wherein
X is F, Cl, Br, I, or CF$_3$SO$_3$.

3. A process according to claim 1, wherein
X is F, and
Y$_1$ is CN, CONH$_2$, COOC$_2$H$_5$, or COCH$_3$.

4. A process according to claim 1, wherein
X is F, and
Y$_1$ is NO$_2$.

5. A process according to any one of the proceeding claims, wherein the substituent Y and Y$_1$ is in the 4-position.

6. A process according to any one of the proceeding claims, wherein the molar ratio of morpholine to substituted benzene is in the range of 10:1 to 1:1.

7. A process according to claim 4, wherein the molar ratio of morpholine to substituted benzene is 1:1.

8. A process according to claim 1, wherein the process is performed in absence of an additional base.

9. A process according to claim 1, wherein the process is performed in the absence of a catalyst.

10. A process according to claim 1, wherein the process is performed under normal pressure and at a temperature range from 20° C. to 130° C.

11. A process according to claim 10 wherein the temperature is about 120° C. when Y$_1$ is CN, CONH$_2$, COOC$_2$H$_5$ and COCH$_3$.

12. A process according to claim 4, wherein the temperature is about 40° C. when Y$_1$ is NO$_2$.

13. A process according to claim 1, wherein the 4-morpholinylbenzene compound is 4-morpholinyl benzoic acid.

14. A process according to claim 13, wherein the process is performed by a one-pot method.

15. The process according to claim 1, wherein the molar ratio of morpholine to substituted benzene is in the range of 7:1 to 1:1.

16. The process according to claim 1, wherein the molar ratio of morpholine to substituted benzene is in the range of 3.5:1 to 1:1.

17. The process according to claim 1, wherein the molar ratio of morpholine to substituted benzene is 1:1.

18. The process according to claim 12, wherein the molar ratio of morpholine to substituted benzene is 1:1.

* * * * *

UNITED STATES PATENT AND TRADEMARK OFFICE
CERTIFICATE OF CORRECTION

PATENT NO. : 6,689,882 B2  
DATED : February 10, 2004  
INVENTOR(S) : W. Tian

Page 1 of 1

It is certified that error appears in the above-identified patent and that said Letters Patent is hereby corrected as shown below:

Column 7,  
Line 25, "formula IIIand" should read -- formula III and --.  
Lines 33-35, delete the structure for formula III and substitute the following structure therefor:

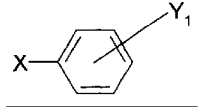

Line 48, "$R^2$, $R^3$" should read -- $R^2$ and $R^3$ --; and "of is" should read -- of --.  
Line 50, "aryl and" should read -- aryl, and --.

Column 8,  
Line 1, "N, O, S" should read -- N, O, and S --.  
Line 4, "Y," should read -- $Y_1$ --.  
Lines 9, 13, 16, 18, 21, 23, 25, 27, 30, 33, 35 and 38, "A" should read -- The --.  
Lines 16-17 and 18-19 (2 instances), "any one of the proceeding claims" should read -- claim 1 --.  
Line 17, "substituent Y and $Y_1$ is" should read -- substituents Y and $Y_1$ are --.  
Line 24, "in absence" should read -- in the absence --.  
Line 32, "and $COCH_3$" should read -- or $COCH_3$ --.

Signed and Sealed this

Fourteenth Day of September, 2004

JON W. DUDAS  
*Director of the United States Patent and Trademark Office*